United States Patent [19]

Butts et al.

[11] 4,285,594
[45] Aug. 25, 1981

[54] OPTICAL SYSTEM FOR DENSITOMETER

[75] Inventors: Gene A. Butts; Samuel Rhine, both of Beaumont, Tex.

[73] Assignee: Helena Laboratories Corporation, Beaumont, Tex.

[21] Appl. No.: 61,201

[22] Filed: Jul. 27, 1979

[51] Int. Cl.³ .................... G01N 21/01; G01N 21/64
[52] U.S. Cl. ........................................ 356/72; 356/73; 356/344
[58] Field of Search ................... 356/72, 73, 418, 432, 356/443, 444, 344

[56] References Cited

U.S. PATENT DOCUMENTS

| | | | |
|---|---|---|---|
| 3,102,202 | 8/1963 | Sweet | 356/443 |
| 3,350,567 | 10/1967 | Strasheim | 250/237 R |
| 3,527,536 | 9/1970 | Alpen | 356/432 |
| 3,655,288 | 4/1972 | Lieberman et al. | 356/418 |
| 3,846,027 | 11/1974 | Hyman et al. | 356/418 |
| 4,005,434 | 1/1977 | Golias et al. | 356/435 |
| 4,040,751 | 8/1977 | Baker et al. | 250/237 R |
| 4,117,338 | 9/1978 | Adrion et al. | 250/461 R |

FOREIGN PATENT DOCUMENTS

| | | | |
|---|---|---|---|
| 1346766 | 2/1974 | United Kingdom | 356/72 |
| 1379405 | 1/1975 | United Kingdom | 356/72 |

*Primary Examiner*—Vincent P. McGraw
*Attorney, Agent, or Firm*—Cullen, Sloman, Cantor, Grauer, Scott & Rutherford

[57] ABSTRACT

An optical system is disclosed for a densitometer which scans an electrophoretically separated sample and provides an output signal for graphical display indicative of the optical density of the scanned sample. The optical system provides storage for a plurality of filter assemblies selectively used depending on the mode of densitometry scanning. It includes a turret assembly, a detector housing, and a lamp support to permit an operator convenient selection capability of a desired filter when scanning in either visible or fluorescent modes of operation. A plurality of optical density and blocking filters are sandwiched between turret plates at spaced radial positions. The plates have aligned openings adjacent to the filter areas to permit light to pass through the filters for detection. Turret barrels and slit assemblies are mounted on one of the plates above the filters to protect the photo-responsive detector from stray light which may be present and to optimize the sensitivity and resolution of the electrophoresis patterns. The plate-filter sandwich unit is rotatably mounted above the detector such that the individual filters are selectively rotated into a position directly above and in alignment with the detector. The turret assembly includes an indexing mechanism and control arrangement to insure that only the visible light source is on when certain filters are above the detector and only the ultra-violet light source is on when other filters are above the detector. A sight alignment and override feature is provided in the optical system such that when the door to the densitometer is open, both the visible and fluorescent light sources are on. Under these conditions, light sources assist the operator in aligning the sample for scanning. Another part of the invention resides in the collimating slit assemblies mounted on the turret assembly which are used for defining the amount of light and the area of the sample seen by the detector in the fluorescent mode.

6 Claims, 3 Drawing Figures

OPTICAL SYSTEM FOR DENSITOMETER

BACKGROUND OF THE INVENTION

The present invention relates in general to densitometers and, more particularly, to an optical system for a graphical display densitometer.

Densitometers are well-known as devices which scan a sample and provide an output signal for graphical display indicative of the optical density of the scanned sample. One well-known use of the densitometer is to scan a sample of blood which has been prepared by the electrophoresis process.

Electrophoresis of blood samples isolates various proteins in the blood, known as albumin, alpha-1 globulin, alpha-2 globulin, beta-globulin and gamma-globulin. The electrophoresis technique separates these proteins from each other and then the sample may be processed or scanned in a densitometer. Each of the proteins exhibits a different light absorption characteristic or pattern and the light absorption patterns are graphically displayed by the densitometer to indicate the presence and quantity of each protein.

In optical density analysis, the amount of light passing through the sample is an inverse logarithmic function of the optical density of the sample. The light transmitted through the sample falls on a photo-responsive element which generates electrical signals having a current proportional to the amount of transmitted light. The current output of the photo-responsive element is, therefore, also a logarithmic function of the optical density which then is converted into analog or time varying signals directly proportional to the optical density pattern of the scanned sample. The analog signals drive a graphic display unit to provide a permanent curve or record of the optical density pattern.

The analog signals, when graphically displayed, exhibit a series of peaks and valleys. In the analysis of blood, the area under the optical density curve and bounded by the two adjacent valleys separated by one peak, is representative of the quantity of each protein in the sample. Each point of the resultant curve is a function of the density of the sample at a corresponding position within the sample. It is a known technique to scan the sample and use an electronic integrator to quantitate the area under the curve and thereby determine the concentration of the sample. An example of a method and apparatus for graphic densitometer display is shown in U.S. Pat. No. 4,005,434 assigned to the assignee of the present invention.

In electrophoresis densitometry, both white light (visible mode) and ultraviolet energy sources (fluorescent mode) are used. A tungsten lamp may be used for transmission densitometry (i.e., using white light) because it emits useful amounts of radiation over the visible spectrum. A low pressure mercury source may be used for the fluorescent mode of operation because it has a strong emission at 366 nm, a wave length efficient for exciting most fluorescent samples. Unlike transmission densitometery, the ultraviolet energy is used to excite the sample. The light emitted by the sample is at a wave length different that the ultraviolet energy. In the fluorescent mode, the light detected and measured is that emitted by the sample.

While a photocell may be used as the detector in the visible mode, it is not satisfactory in the fluorescent mode because the intensity of the fluorescence is low in most cases. Thus, a photomultiplier tube or equivalent type detector is used because it has the high sensitivity necessary to detect weak fluorescence. The photomultiplier tube detector may also be optimized for operation in the visible spectrum.

Filters are required in both the visible and fluorescent modes of operation when using a photomultiplier tube in order to protect the detector. For fluorescent densitometry, the ultraviolet source is placed on the same side of the sample as the detector because otherwise some of the support media would block or filter ultraviolet light and the sample would not be excited if the light were on the opposite side. Because of this arrangement of source and sample for fluorescent densitometry, a filter is required to block ultraviolet energy from the exciting source below a certain level from reaching the detector. Further, the photomultiplier detector is so sensitive that in the visible mode, an optical density filter may be necessary to protect the photomultiplier detector if the sample is not dense enough such that the detector will remain in the linear region of operation and not become saturated. Thus, several types of filters are required when transmission and fluorescent densitometry are incorporated in one machine and when a single sensitive detector such as a photomultiplier tube is used.

A problem has existed in efficiently handling the plurality of filters required for the fluorescent and visible modes while insuring that the filter selected matches the particular mode of operation. A typical method of operation has been that the operator manually changes the filters depending upon whether transmission or fluorescent densitometry is desired. This is unacceptable because the manual handling of the filters adversely affects the quality of the detected light. Further, the filters may become misplaced or damaged thereby making them unavailable when desired. Thus, the present optical system has been devised such that the operator may conveniently select a desired filter for either mode of operation, and the filters are always available to be used when needed.

SUMMARY OF THE INVENTION

In accordance with the present invention, an optical system is provided for storing a plurality of filter assemblies which are selectively used depending on the mode of densitometry scanning.

The specially designed optical system includes a turret assembly, a detector mounting housing, and a lamp support. The system permits an operator to conveniently select a desired filter when scanning in either the fluorescent or visible modes.

The turret assembly includes a plate-filter sandwich unit comprising a top plate and a bottom plate secured together with a plurality of optical density and ultraviolet blocking filters sandwiched between them at spaced radial positions. The plates have aligned circular openings adjacent to the filter areas to permit light to pass through the filters for detection. Turret barrels are mounted to the top plate above the optical density filters to protect the photo-responsive detector from stray light which may be present. In a like manner, slit assemblies are mounted above the ultraviolet blocking filters to optimize the sensitivity and resolution of the electrophoresis patterns in the fluorescent mode of operation.

The bottom turret plate has a diameter greater than the top plate so that indicia may be put on the bottom plate periphery to identify the filter locations. The underside of the bottom plate also has indexing detents equal to the number of filter positions and switch depressions which cooperate with switches to turn the tungsten and mercury light sources on and off depending on the mode being used.

The turret assembly further includes a pivot post assembly which rotatably amounts the plate-filter sandwich unit and also mounts the base of the photomultiplier tube detector. A spring biased detent mechanism integral with the pivot post assembly cooperates with the indexing detents in the bottom turret plate for holding a selected filter in position above the photomultiplier tube detector.

The detector mounting housing completely encases the photomultiplier tube except for an opening through its top surface which permits radiation to impinge on the photomultiplier tube. The turret assembly is mounted to the detector housing such that the individual filters are rotatable into a position directly above and in alignment with the detector mounting opening. In the disclosed embodiment, a desired filter is rotated manually into position above the detector by the operator and held in that position by the detent mechanism. It is also within the scope of the present invention to provide a motor or the like to automatically rotate the turret above the detector.

An ultraviolet lamp support is mounted on the detector mounting housing adjacent to the detector mounting opening for the fluorescent mode of operation. Further, switches are mounted to the detector housing and each switch has a spring biased operator protruding from it which cooperates with a respective depression in the bottom turret plate. When the operators are out and into engagement with the plate depressions, the ultraviolet lamp is on and the visible lamp is off. When the operators are depressed by the turret plate and out of engagement with the plate depressions, the visible light source is on and the ultraviolet light source is off. Thus, the optical system of the present invention prevents the operator from using an ultraviolet filter in the visible mode or vice versa.

A sight alignment and override feature is provided in the optical system to assist the operator in aligning the sample for scanning. It is difficult for an operator to align a sample within the densitometer for scanning because there is not always adequate illumination for that procedure. To overcome this difficulty, a switch has been provided which cooperates with the door to the densitometer, and when the door is open, both the visible and fluorescent light sources are switched on. Thus, the door switch overrides the densitometry mode selected while the door is open and the operator is working to situate the sample for scanning. Under these conditions, the visible light source, in particular, assists the operator in aligning the sample for scanning by providing the needed illumination.

Another part of the present invention resides in the collimating slit assemblies mounted on the turret assembly and used for defining the amount of light and the area of the sample seen by the detector in the fluorescent mode. The slit assemblies include upstanding inner collimator plates which define the ends of a slit opening. The inner collimator plates are held between outer collimator plates which define the sides of the slit opening. A small slit opening is provided when it is desired to have greater freedom in selecting the area of the sample to be scanned and when higher resolution is desired. A large slit is provided and may be necessary where, for example, the sample emission is relatively low and thus the amount of light passed by the smaller slit may not be enough to keep the detector in a linear region of operation.

Other advantages and meritorious features of the optical system will be more fully understood from the following description of the preferred embodiment, the appended claims, and the drawings, a brief description of which follows.

DESCRIPTION OF THE PREFERRED EMBODIMENT

Figure 1:
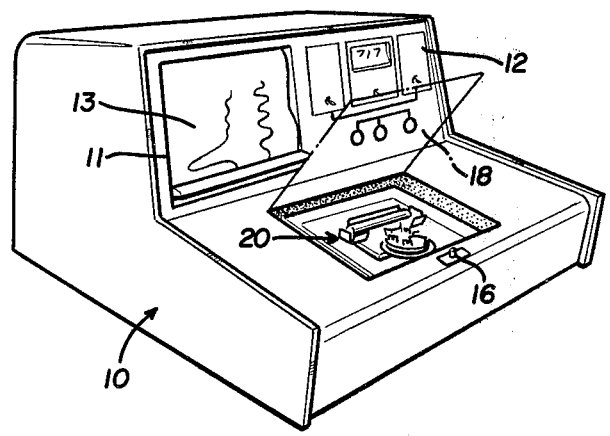
FIG. 1 is a perspective illustration of a densitometer having the optical system of the present invention.
Figure 3:
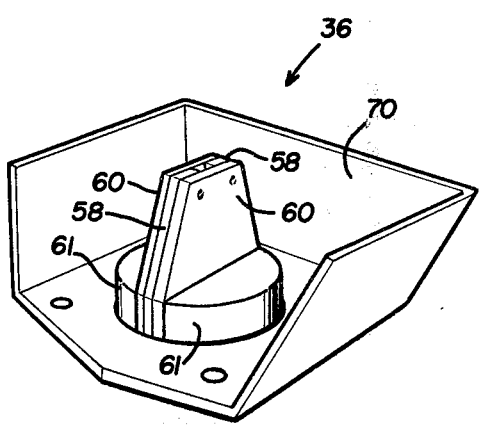
FIG. 3 is a perspective detailed view of one slit assembly utilized during the fluorescent mode.
Figure 2:
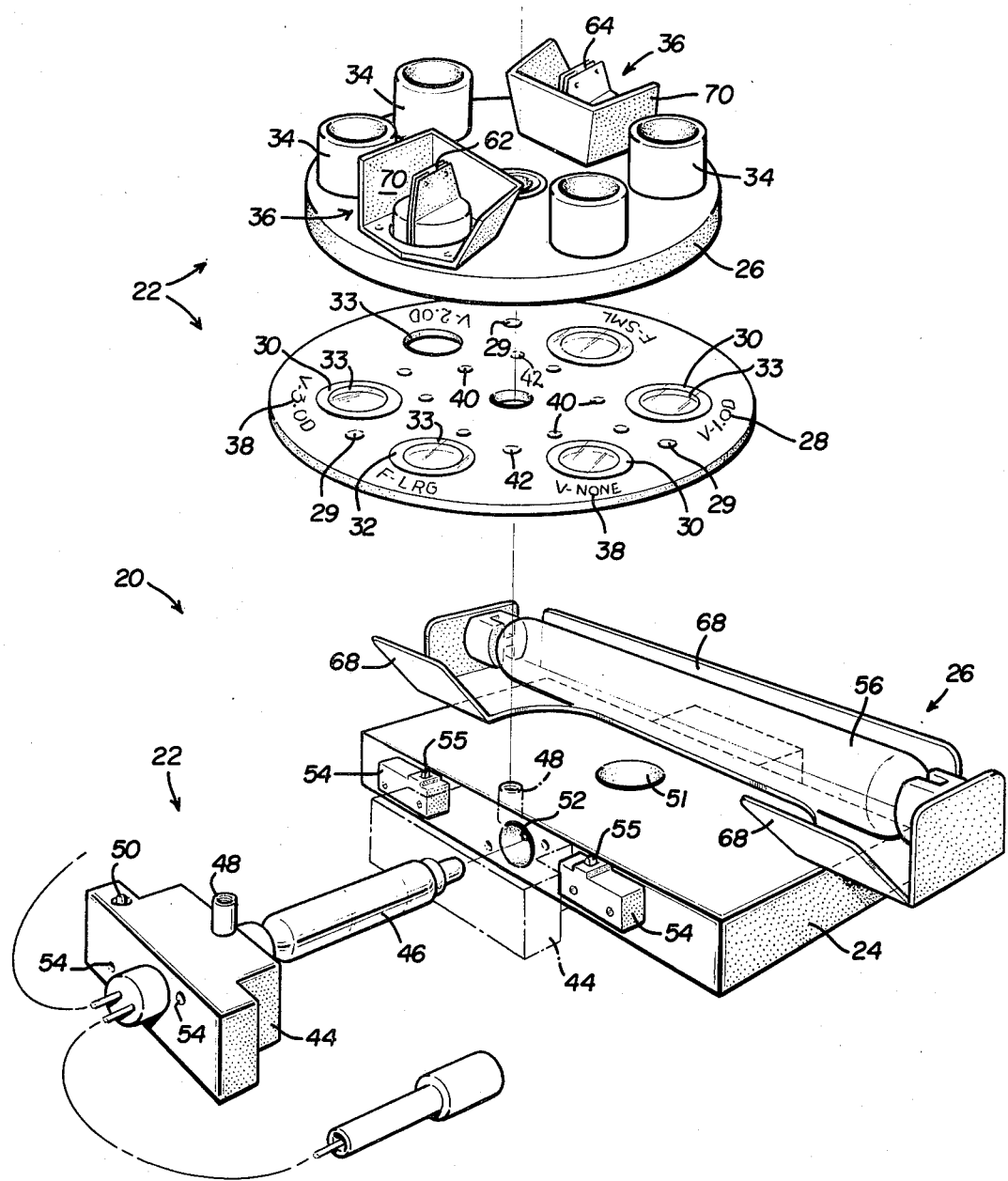
FIG. 2 is a perspective view of the individual components in the optical system including an illustration of their assembly.

With reference to the drawings, there is illustrated a densitometer 10 including a display area 11 and a control panel 12. The densitometer includes scanning means (not shown) for generating optical density signals of a sample which has been prepared by the electrophoresis technique. An example of a conventional scanning means is illustrated in U.S. Pat. No. 4,005,434 assigned to the assignee of the present invention, which is incorporated by reference herein.

The scanning means broadly includes a light source which may be fluorescent or incandescent, depending upon the type of sample utilized. The light transmitted through the sample (i.e., transmission densitometry) or emitted by the sample (i.e., fluorescent densitometry) is detected by a photo-responsive element, and the current generated by the photo-responsive element is proportional to the amount of light transmitted by or through the sample. Thus, a sample is scanned through an optical path defined by the light source and photo-responsive element as is well known.

As is conventional, the sample is held in a movable carriage which is moved or scanned through the optical path. The output of the photo-responsive device is ultimately displayed on a cross-hatched or graph paper in the form of a curve illustrated as 13.

In accordance with the present invention and as illustrated, an optical system 20 is provided for storing a plurality of filter assemblies which are selectively used depending on the mode of densitometry scanning.

The optical system 20 includes a turret assembly 22, a detector mounting housing 24, and a lamp support 26. The system permits an operator to conveniently select a desired filter when scanning in either the fluorescent or visible modes of operation.

The turret assembly 22 includes a plate-filter sandwich unit comprising a top plate 26 and a bottom plate 28 secured together by set screws which pass through openings 29 in bottom plate 28. A plurality of optical density filters 30 and ultraviolet blocking filters 32 are sandwiched between plates 26 and 28 at spaced radial positions. The plates 26, 28 have aligned circular openings 33 adjacent the filter areas to permit light to pass through the filters for detection.

Elongated, cylindrical turret barrels 34 are mounted in the top plate 26 above the optical density filters 30 to protect the photo-responsive detector from stray light which may be present during the visible mode of operation. In a like manner, slit assemblies 36 are mounted above the ultraviolet blocking filters 32 to optimize the sensitivity and resolution of the electrophoresis patterns in the fluorescent mode of operation.

The bottom turret plate 28 has a diameter greater than the top plate 26 so that indicia 38 may be put on the bottom plate periphery to identify the filter locations. The underside of the bottom plate 28 also has indexing detents 40 equal to the number of filter positions and switch depressions 42 which cooperate with switches to turn the tungsten and mercury light sources on and off depending on the mode being used.

The turret assembly 20 further includes a pivot post assembly 44 which rotatably mounts the plate-filter sandwich and the base of a photomultiplier detector 46. The pivot assembly 44 includes a pivot post 48 on which the plate-filter sandwich unit is rotatably mounted. A spring-biased detent mechanism 50 is integral with the pivot post assembly 44 and cooperates with the indexing detents 40 on the bottom turret plate 28 for holding a selected filter in position above the photomultiplier detector 46.

The pivot post assembly is mounted to a detector mounting housing 24 which completely encases the photomultiplier tube 46 except for an opening 51 through its top surface that permits radiation to impinge on the photomultiplier tube. The photomultiplier tube 46 is inserted within opening 52 in the detector housing and pivot post assembly 44 is secured to the housing by bolts 54. The turret assembly 22 is mounted to the detector housing 24 such that the individual filters 30 and 32 are rotatable into a position directly above and in alignment with the detector mounting opening 51. In the disclosed embodiment, a desired filter is rotated manually to position above the detector 46 by the operator and held in that position by the detent mechanism 50 which cooperates with indexing detents 40. It is also within the scope of the scope of the present invention to provide a motor or the like to automatically rotate the turret above the detector.

A fluorescent lamp support 26 is mounted on the detector mounting housing 24 adjacent to the detector mounting opening 51 for the fluorescent mode of operation. Single pole switches 54 are mounted to the detector housing 24, and each switch has a spring-biased operator 55 protruding from it which cooperates with a respective depression 42 in the bottom turret plate 28. When the operators are out and into engagement with the plate depressions 42, the fluorescent lamp 56 is on and the visible lamp (not shown) is off. When the operators 55 are depressed by the turret plate 28 and out of engagement with the depressions 42, the visible light source is on and the fluorescent lamp 56 is off. Thus, the optical system of the present invention prevents the operator from using an ultraviolet filter 32 in the visible mode or an optical density filter 30 in the fluorescent mode.

A sight alignment feature is provided in the optical system to assist the operator in aligning the sample for scanning. A switch 16 (FIG. 1) cooperates with the door 18 to the densitometer 10. When the door is open as illustrated in FIG. 1, switch 16 overrides the densitometry mode selected and turns both the visible (not shown) and fluorescent 56 light sources on. The visible light source, in particular, provides needed illumination so that the operator can properly align the sample to be scanned on the movable carriage. When the door is closed, a desired mode of denistometry scanning may be selected and either the visible or fluorescent light sources will be on as heretofore discussed.

Another part of the present invention resides in the collimating slit assemblies 36 mounted on the turret assembly 22 and used for defining the amount of light and the area of the sample seen by the detector in the fluorescent mode. The slit assemblies 36 include upstanding near collimator plates 58 which define the ends of a slit opening. The inner collimator plates 58 are held between outer collimator plates 60 by ring members 61. Collimator plates 60 define the sides of the slit opening. A small slit opening 62 is used when it is desired to have greater freedom in selecting the area of the sample to be scanned and when higher resolution is desired. A larger slit opening 64 may be necessary where, for example, the sample emission is relatively low and thus the amount of light passed by the smaller slit 62 may not be enough to keep the detector 46 in a linear region of operation.

The fluorescent lamp support 26 includes upstanding mirrored surfaces 68, and mirrored surfaces 70 also surround each slit assembly so that higher light illumination may be provided to the sample.

In operation, a sample is held in a movable carriage (not shown) which is moved or scanned through an optical path. A light source is used which may be fluorescent or incandescent depending on the type of sample utilized. Light is transmitted through the sample or emitted by the sample, and the transmitted or emitted radiation is detected by photomultiplier tube 46 after it has passed through one of the filters 30 and 32. The filter above the photomultiplier tube is indicated by the indicia 38 directly across from it. The indicia "V" indicates visible and "None", "1.0D", "2.0D", and "3.0D" indicate the units of optical density. "F" indicates the fluorescent mode of operation and "LRG" and "SML" signify that either large slit opening 64 or small slit opening 62 is being used.

To change filters, the operator rotates the plate-filter turret to the desired position, and it is held there by the detent mechanism 50. The proper light source is turned "on" automatically as the turret is rotated. Thus, the operator may conveniently select a desired filter for either mode of densitometry scanning.

It will be apparent to those skilled in the art that the foregoing disclosure is exemplary in nature rather than limiting, the invention being limited only by the appended claims.

We claim:

1. An optical system for use in a densitometer which generates optical density signals for a sample prepared electrophoretically, said optical system including:

light generating means, said light generating means including a visible light source for a transmission densitometry mode of operation and a fluorescent light source for a fluorescent mode of operation;

a turret assembly having a top plate and a bottom plate secured together as a unit with a plurality of filters sandwiched between said top and bottom plate at spaced radial positions, said plates having aligned openings above and below said filters to permit light to pass through said filters for detection, said plate-filter unit being rotatably mounted on a post assembly;

a photo-responsive detector;

said turret assembly including said plate-filter unit, post assembly, and photo-responsive detector being mounted to a housing, said detector being substantially encased within said housing and said housing having an opening to permit light radiation to impinge on said detector; and said plate-filter unit being selectively rotatable above said opening such that a desired filter is rotated into position above and in alignment with said detector to optimize the resolution of the light detected by said photo-responsive detector;

said turret assembly having visible light filters and fluorescent light filters, first switch means mounted to said housing, said first switch means cooperating with said plate-filter unit to turn off said fluorescent light source except when a fluorescent light filter is in alignment with said detector, said first switch means including at least one spring-biased operator which is engageable with and extendable into a depression in said bottom plate when a fluorescent light filter is aligned with said detector thereby turning on said fluorescent light source, said operator being depressed by said bottom plate and out of engagement with said depression to turn off said fluorescent light source when said visible filters are aligned with said detector; and turret barrels mounted to said plate-filter unit above said visible light filters to protect said detector from stray light which may be present during said transmission mode of operation and slit assemblies mounted to said plate-filter unit above said fluorescent light filters to define the amount of light and the area of the sample seen by the detector in the fluorescent mode of operation.

2. The optical system as defined in claim 1 wherein said slit assemblies provide slit openings of at least two sizes, a relatively small slit opening being provided when it is desired to have greater freedom in selecting the area of the sample to be scanned and a larger slit opening being provided to permit sufficient light impinging on said detector for keeping said detector in a linear region of operation.

3. The optical system as defined in claim 2 wherein each said slit assembly includes upstanding inner collimator plates which define the ends of a slit opening, said inner collimator plates being held between outer collimator plates which define the sides of the slit opening.

4. The optical system as defined in claim 1 wherein said bottom plate having a diameter greater than said top plate, identifying indicia being placed on the periphery of said bottom plate to identify the filter located above said detector.

5. The optical system as defined in claim 1 wherein said bottom plate having detents equal to the number of filter positions, a spring-biased detent mechanism mounted to said post assembly and cooperating with said detents for holding a selected filter in position above said detector.

6. The optical system as defined in claim 1 wherein said densitometer includes a pivotable door which permits an operator access into said densitometer, second switch means cooperating with said door, said second switch means turning said visible and fluroescent light sources on when said door is open to provide illumination to assist in operator in aligning said sample for scanning.

* * * * *